United States Patent
Kim

[19]
[11] Patent Number: 6,023,663
[45] Date of Patent: Feb. 8, 2000

[54] METHOD AND APPARATUS FOR INSPECTING A SOLDER JOINT USING A CORRELATION NEURAL NETWORK

[75] Inventor: Jong-Hyeong Kim, Sungnam, Rep. of Korea

[73] Assignee: Samsung Electronics Co., Ltd., Suwon, Rep. of Korea

[21] Appl. No.: 08/833,451

[22] Filed: Apr. 7, 1997

[30] Foreign Application Priority Data

Apr. 8, 1996 [KR] Rep. of Korea ...................... 96-10514

[51] Int. Cl.[7] ................................................ G06F 17/00
[52] U.S. Cl. ................................. 702/81; 702/40; 706/20; 706/25; 706/40; 382/150
[58] Field of Search ................................. 702/81, 34, 35, 702/40, 124, 126, 172, 183, 184, 189, 198; 250/559.34, 559.42, 559.43, 559.45; 324/717, 718; 228/179.1, 180.1, 180.21, 180.22; 364/468.17; 382/147, 149, 150, 156–160, 164, 165; 348/125, 126, 131, 133, 266, 269, 277; 356/237.1, 394, 384, 376; 706/20, 25, 41, 908, 916, 921, 40

[56] References Cited

U.S. PATENT DOCUMENTS

| | | | |
|---|---|---|---|
| 5,245,671 | 9/1993 | Kobayashi et al. | 382/150 |
| 5,548,697 | 8/1996 | Zortea | 382/159 |
| 5,598,345 | 1/1997 | Tokura | 382/150 |
| 5,751,910 | 5/1998 | Bryant et al. | 382/147 |
| 5,787,408 | 7/1998 | Deangelis | 706/20 |

*Primary Examiner*—Hal Wachsman
*Attorney, Agent, or Firm*—Jones Volentine, LLP

[57] ABSTRACT

A solder joint inspection process and system includes using a correlation values to classify the shape of the solder joint. The solder joint is illuminated by a multiple colors, and the image of the solder joint is captured. This multiple color image is then converted into a plurality of one-dimensional vectors. Each one-dimensional vectors sequence is for one color of the multi-color illumination and for a one-dimensional spatial extent. Correlation values among all combinations of the one-dimensional vector sequences are computed and used for training an automatic solder joint shape classifier.

19 Claims, 12 Drawing Sheets

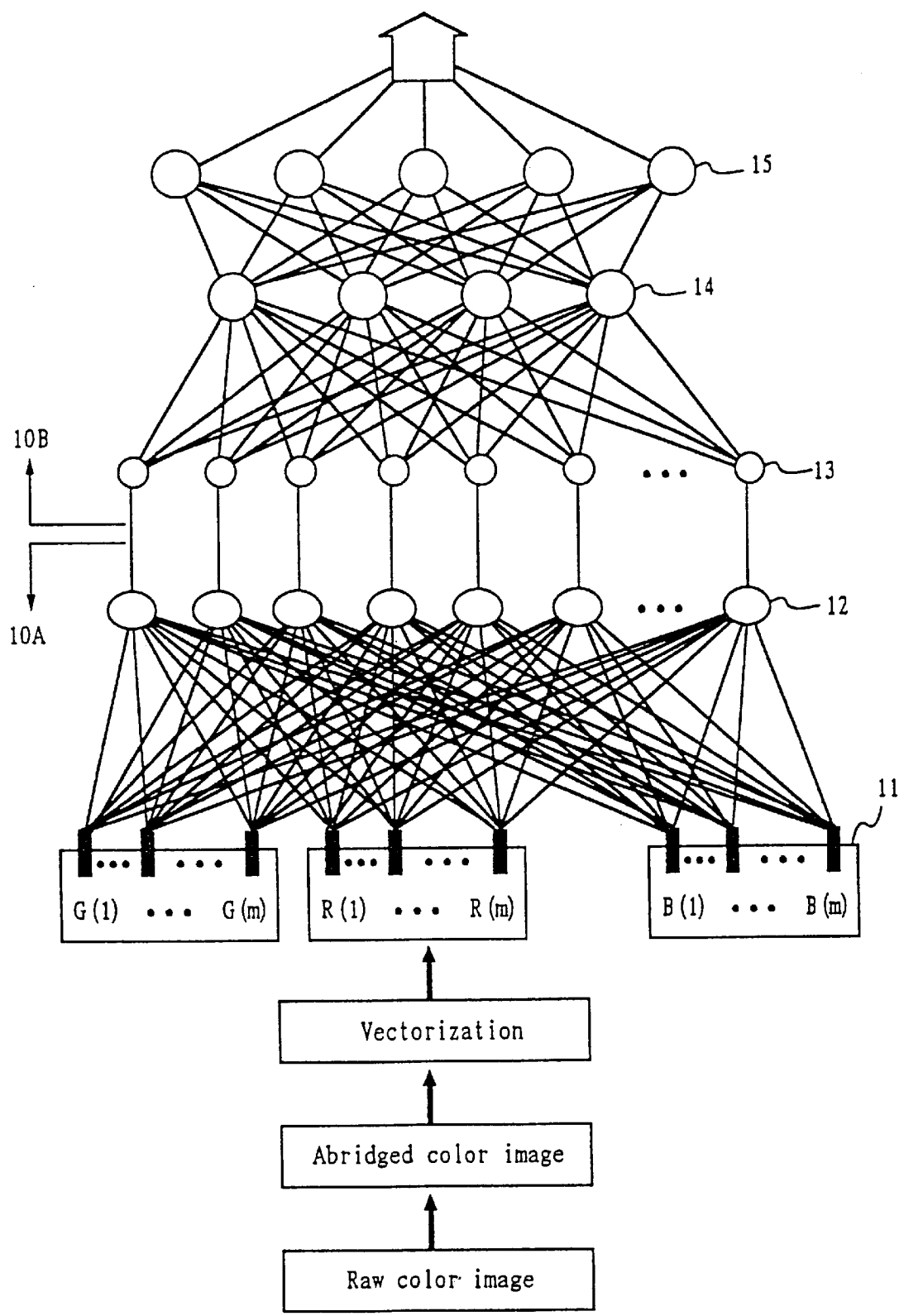

Raw image (Io)

Abridged image (Ic)

FIG. 7
| solder joint classification | 3-D shape | color pattern |
|---|---|---|
| insufficient soldering | 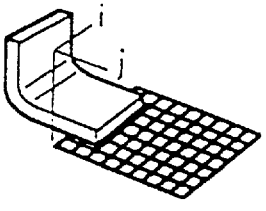 | 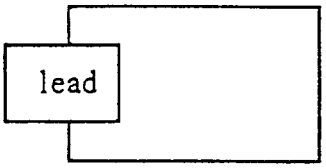 |
| insufficient but acceptable soldering | 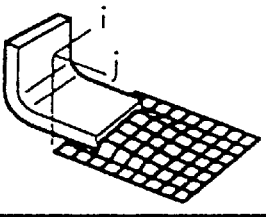 | 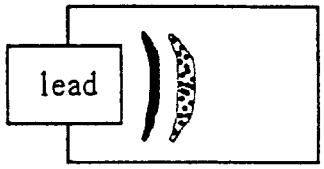 |
| acceptable soldering | 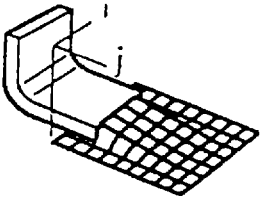 | 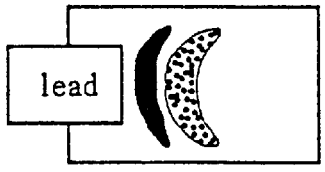 |
| excessive but acceptable soldering | 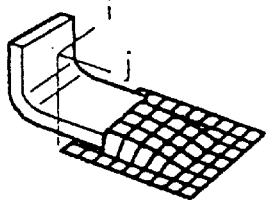 | 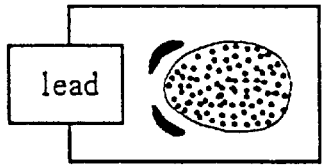 |
| excessive soldering | 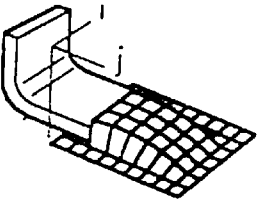 | 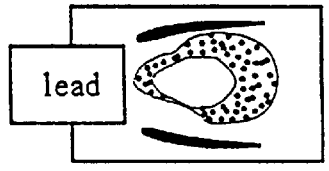 |

FIG. 8A i =     1     2     3     4     5    :column number

| 0 | G | R | 0 | B |
|---|---|---|---|---|
| G | 0 | R | R | B |
| G | 0 | R | R | B |
| B | 0 | R | 0 | B |

|     | number of input nodes | number of output nodes | number of hidden layers | number of nodes in H and L | learning rate | momentum inertia |
| --- | --- | --- | --- | --- | --- | --- |
| (a) | 20 | 5 | 0 | 0 | 0.3 | 0.2 |
| (b) | 20 | 5 | 1 | 5 | 0.3 | 0.2 |
| (c) | 20 | 5 | 1 | 10 | 0.7 | 0.5 |
| (d) | 20 | 5 | 2 | 4, 4 | 0.7 | 0.5 |

|     | number of input nodes | number of output nodes | number of hidden layers | number of nodes in H and L | learning rate | momentum inertia |
|-----|---|---|---|---|---|---|
| (a) | 44 | 5 | 0 | 0 | 0.7 | 0.5 |
| (b) | 44 | 5 | 1 | 5 | 0.7 | 0.5 |
| (c) | 44 | 5 | 1 | 10 | 0.7 | 0.5 |
| (d) | 44 | 5 | 2 | 4, 4 | 0.7 | 0.5 |

|     | number of input nodes | number of output nodes | number of hidden layers | number of nodes in H and L | learning rate | momentum inertia |
|-----|---|---|---|---|---|---|
| (a) | 76 | 5 | 0 | 0 | 0.7 | 0.5 |
| (b) | 76 | 5 | 1 | 5 | 0.7 | 0.5 |
| (c) | 76 | 5 | 1 | 10 | 0.7 | 0.5 |
| (d) | 76 | 5 | 2 | 4, 4 | 0.7 | 0.5 |

METHOD AND APPARATUS FOR INSPECTING A SOLDER JOINT USING A CORRELATION NEURAL NETWORK

BACKGROUND OF THE INVENTION

1. Field of the Invention

The present invention relates to a method and apparatus for inspecting a solder joint of a printed circuit board (PCB) and more particularly, to a method and apparatus for inspecting a solder joint using a correlation neural network, in which solder joint images are effectively classified regardless of positional shift within a pre-defined window, a smaller memory storage is required for synaptic weights, and a learning rate is improved. The memory improvements are achieved by using geometric correlation terms to represent the spatial relations of red, green and blue color patterns in an effective manner. The experiences of a human inspector were utilized in building the architecture of this neural network and those experiences have reduced the classification burden from that of a back propagation (BP) network, thereby improving the overall classification performance.

2. Description of the Related Art

Surface-mounting technology (SMT) in printed-circuit board assembly processes has been vigorously developing to keep pace with the new electrical products' trend toward the miniaturization of components and denser packing of boards. In the commercial PCB assembly process using SMT, a great deal of effort has been directed toward quality control which is crucial to ensure reliability in end products. However, one hundred percent accurate inspection is difficult for a human inspector due to high production rates and the tedious nature of manual inspection. For these reasons, the development of automatic visual inspection systems for solder joints has drawn increasing attention with increasing demand for reliability in end products.

Automated solder joint inspection, however, has been considered difficult due to the sheen of the solder joint surface and the complexity of solder joint shapes. These two effects make it difficult to extract three-dimensional (3-D) information of the solder joint surface. Specular reflections from the high sheen surface of the solder joint may appear, disappear, or change their patterns abruptly even with small changes in viewing direction. Furthermore, a distant point illumination can not produce smooth shading on the specular solder joint surface, because light is reflected in a single direction. Although many researchers have tackled this challenging problem, only a few commercial systems using sophisticated illumination sources, sensors and mechanisms are on the market. The wide variety of the solder joint shapes is a barrier to developing an automatic solder joint inspection system. Solder joint shapes tend to vary greatly in three dimensions, depending on soldering conditions such as the amount of solder paste cream and the heating level during the soldering process.

To extract three-dimensional shape information for solder joint inspection, a tiered-color illumination system is used. The tiered-color illumination system, which consists of red, green, and blue color circular lamps and one color camera, is well known in the art. Lit by such a system, variations in inclination of the solder joint surface reveal three patterns of highlight color, that is, one each in red, green and blue. The spatial relations of the highlight color patterns provide visual cues for inferring a three-dimensional shape of the inspected surface. However, due to the complexity of the solder joint shapes, the geometric characteristics of the color patterns, imaged by the tiered-color illumination system, also exhibit substantial variability. This makes it difficult to classify the color patterns of the solder joints into distinct groups. Even if the solder joints belong to the same class of acceptable quality, their shapes are different from each other to some extent. In addition, there is no quantitative reference of solder joint shapes to decide their soldering quality. Classification criteria for solder joint inspection usually depend on a human's skillful experience which is difficult to program. Due to this complexity, careful attention is required to define suitable visual features and to determine classification criteria.

During the last several years, artificial intelligent approaches have been applied to many problems due to their ability to learn from a human's experience. Multi-layered neural networks have been used vigorously during this trend. However, when the input data space is too complex to determine decision surfaces for classification, or when input data are shifted in position, etc., application of the multi-layered neural network suffers. In these situations, the convergence rate of the generalized-delta rule (G.D.R.) is often unacceptably low, and often the classification may not be successful.

SUMMARY OF THE INVENTION

Therefore, the present invention has been made in view of the problems occurring in the related art, and an object of the present invention is to provide a method and apparatus for inspecting a solder joint using a correlation neural network, in which solder joint images are effectively classified regardless of positional shift thereof within a pre-defined window.

Another object of the present invention is to provide a method and apparatus for inspecting a solder joint using a correlation neural network, in which the experiences of a human inspector are utilized in building the architecture of a neural network to reduce the classification burden of a back propagation (BP) network, thereby improving the overall classification performance.

According to one aspect of the present invention, there is provided an apparatus for inspecting a solder joint, the apparatus comprising: a solder joint image extracting means for extracting three-dimensional image information of a solder joint subjected to multi-color illumination; and a solder joint shape classifying means for learning a classification hierarchy of solder joint images by using a training set of said solder joint images classified into said classification hierarchy by a human solder joint inspector, and for applying said learned classification hierarchy to said extracted image information.

According to another aspect of the present invention, said solder joint image extracting means comprises: a multi-color illuminator for emitting at least three colors of light, each color at a different incident angle to a solder joint inspection area; a color camera for capturing color images reflected from said solder joint inspection area with a digital image pickup device; and a color image grabber for grabbing a plurality of color frames, one frame for each of the colors from an output of said color camera.

According to another aspect of the present invention, the solder joint shape classifying means comprises a correlation neural network for converting the plurality of color frames into a plurality of one-dimensional vector sequences, for calculating correlation values among the vector sequences, and for learning synaptic weights to apply to the correlation values to produce the classification hierarchy determined by the human solder joint inspector, and for applying previously learned synaptic weights to the correlation values to produce an automatic classification within said classification hierarchy.

According to another aspect of the present invention, said multi-color illuminator comprises: three circular, high-frequency neon lamps respectively emitting green light, red light, and blue light, which are coaxially tiered in sequence of decreasing diameter and in sequence of increasing distance from a plane containing the solder joint inspection area.

According to other aspects of the present invention, the green, red, and blue circular, high frequency neon lamps have diameters of about 130 mm, about 70 mm, and about 40 mm, respectively, and are positioned to have incident angles at the solder joint inspection area of about 70°, about 40° and about 20° from a pointing axis of the color camera, respectively.

According to another aspect of the present invention, the correlation neural network comprises: a preprocessing module for calculating correlation values among the plurality of one-dimensional vector sequences derived from the plurality of color frames within one image; and a trainable module for learning synaptic weights to apply to the correlation values to produce the classification hierarchy determined by the human solder joint inspector, and for applying previously learned synaptic weights to the correlation values to produce an automatic classification within the classification hierarchy.

According to another aspect of the present invention, a method for inspecting a solder joint is provided, the method comprising illuminating a solder joint with multiple-color light emitters distributed in three-dimensions; extracting a multi-colored image of said solder joint; determining a classification hierarchy of the solder joints by a human solder joint inspector; and classifying solder joint images by training a solder joint shape classifier to associate the extracted images of the solder joint with the classification hierarchy, and by applying the trained solder joint classifier to the extracted images of the solder joint.

According to another aspect of the present invention, the step of illuminating the solder joint comprises the step of placing different color illuminators at different angles of incidence to a solder joint inspection area.

According to another aspect of the present invention, the step of placing different color illuminators at different angles of incidence to a solder joint inspection area comprises the step of: placing three circular light emitters of green, red, and blue light, coaxially in order of decreasing diameter and in sequence of increasing distance from the solder joint inspection area.

According to another aspect of the present invention, the step of extracting of a multi-colored image of the solder joint comprises the steps of: capturing a digital image of light reflected the solder joint inspection area; and grabbing a plurality of color frames from the digital image.

According to another aspect of the present invention, the step of classifying solder joint images comprises the step of: operating a correlation neural network to learn to associate the extracted images of the solder joint with the classification hierarchy, and to act on the extracted images of the solder joint to produce an automatic classification within the classification hierarchy.

According to another aspect of the present invention, the step of operating of the correlation neural network comprises the steps of: preprocessing the multi-colored image of the solder joint into one dimensional vector sequences and calculating correlation values among the vector sequences; training synaptic weights of a trainable module to convert the correlation values into the classification hierarchy by comparing the network output to classifications made by the human solder joint inspector; and, applying the learned weights to classify the image of the solder joint within the classification hierarchy.

According to another aspect of the present invention, the preprocessing comprises the steps of: (a) abridging the multi-colored image into an abridged image which has a size smaller than the multi-colored image; (b) expressing each column of pixels of the abridged image as the one-dimensional vector sequence; and (c) forming the correlations by calculating cross-correlation and auto-correlation values among the one-dimensional vectors sequences.

According to another aspect of the present invention, the training comprises the steps of: (d) calculating an error for a sample pattern and an average system error by comparing network output values with target classification values defined by the classification hierarchy; and (e) training the synaptic weights of the trainable module by using the sample error and the average system error.

According to another aspect of the present invention, the step (a) sets one pixel of said abridged image to be equivalent to a window of a raw image, where the window is L pixels wide by K pixels high (L×K), and the raw image is one color of the multi-colored image of the solder joint, and then the one pixel of the abridged image is described by $$I_c(i,j) = 1, \text{ if } \sum_{l=0}^{L}\sum_{k=0}^{K} I_0(u_0+l, v_0+k) > \tau$$
$$= 0, \text{ else}$$

where, $(u_0, v_0)$ is a position of an initial pixel of the raw image within the one pixel at position $(i, j)$ of the abridged image, and $\tau$ is a threshold value which is determined by a network designer; wherein the step (b) rewrites green, red and blue abridged images as the one-dimensional vector sequences which are denoted by $$\{G(i)|i=1, \ldots, m\}$$
$$\{R(i)|i=1, \ldots, m\}$$
$$\{B(i)|i=1, \ldots, m\}; \text{ and,}$$

wherein the step (c) calculates spatial correlation values of certain combinations of color vector sequences by using a correlation node, the output of the correlation node being described by (output of correlation node)

$$= f[C_1(\cdot), C_2(\cdot), d] = \sum_{i=0}^{m-d} C_1(i) \cdot C_2(i+d)$$

where $\{C_1(i)|i=1, \ldots, m\}$ and $\{C_2(i)|i=1, \ldots, m\}$ are the two vector sequences to be calculated, and m is the maximum number of elements in each of the vector sequence.

According to another aspect of the present invention, said step (d), the output $O_j$ of a node j is activated by using sigmoid function as described by $$O_j = \frac{1}{1+e^{-(net_j+\sigma_j)/\sigma_o}}$$

where $net_j$ is the net input to a node in layer j, the parameter $\sigma_j$ serves as a threshold or bias, and $sigma_o$ is a shape parameter; the output error $E_p$ for each sample pattern is taken as $$E_p = \frac{1}{2}(t_p - o_f)$$

where $t_p$ denotes the target classification values, and $o_f$ denotes the network output;

and the average system error E is defined as $$E = \frac{1}{2P}\sum_p (t_p - o_f)^2$$

where P is a total number of the multi-colored images of the solder joints in a training set, and subscript p denotes each multi-colored image of the solder joints in the training set.

According to still another aspect of the present invention, in the step (e), the synaptic weights are trained when convergence is achieved using generalized-delta rule according to the following equation $$\Delta w_{kj} = -\eta \frac{\partial E}{\partial W_{kj}} + \alpha$$

where $\eta$ is the learning rate, alpha is a momentum term, and $W_{kj}$ is the synaptic weight for the output from network node k when used as input to network node j.

By the features of the present invention, solder joint images can be effectively classified regardless of shift in position within a pre-defined window, and the experiences of human inspector is utilized to build the architecture of a network to reduce the classification burden below that required by a BP network. As a result, the whole classification performance of the network is improved.

BRIEF DESCRIPTION OF THE DRAWINGS

The above and other objects, and other features and advantages of the present invention will become more apparent by describing in detail one or more preferred embodiments thereof, taken in conjunction with the attached drawings, in which:

FIG. 3 is a diagram schematically illustrating the architecture of a correlation neural network of FIG. 1;

FIG. 7 shows typical synthetic examples of three-dimensional shapes and the corresponding highlight color patterns in window images classified by their soldering qualities;

FIGS. 8A and 8B show an example of the abridged color image with 4×5 pixel size and vector sequences thereof, respectively;

DETAILED DESCRIPTION OF THE PREFERRED EMBODIMENTS

Hereinafter, a method and apparatus for inspecting a solder joint using a correlation neural network in accordance with the embodiments of the present invention, will be fully described with reference to the drawings.

Figure 1:
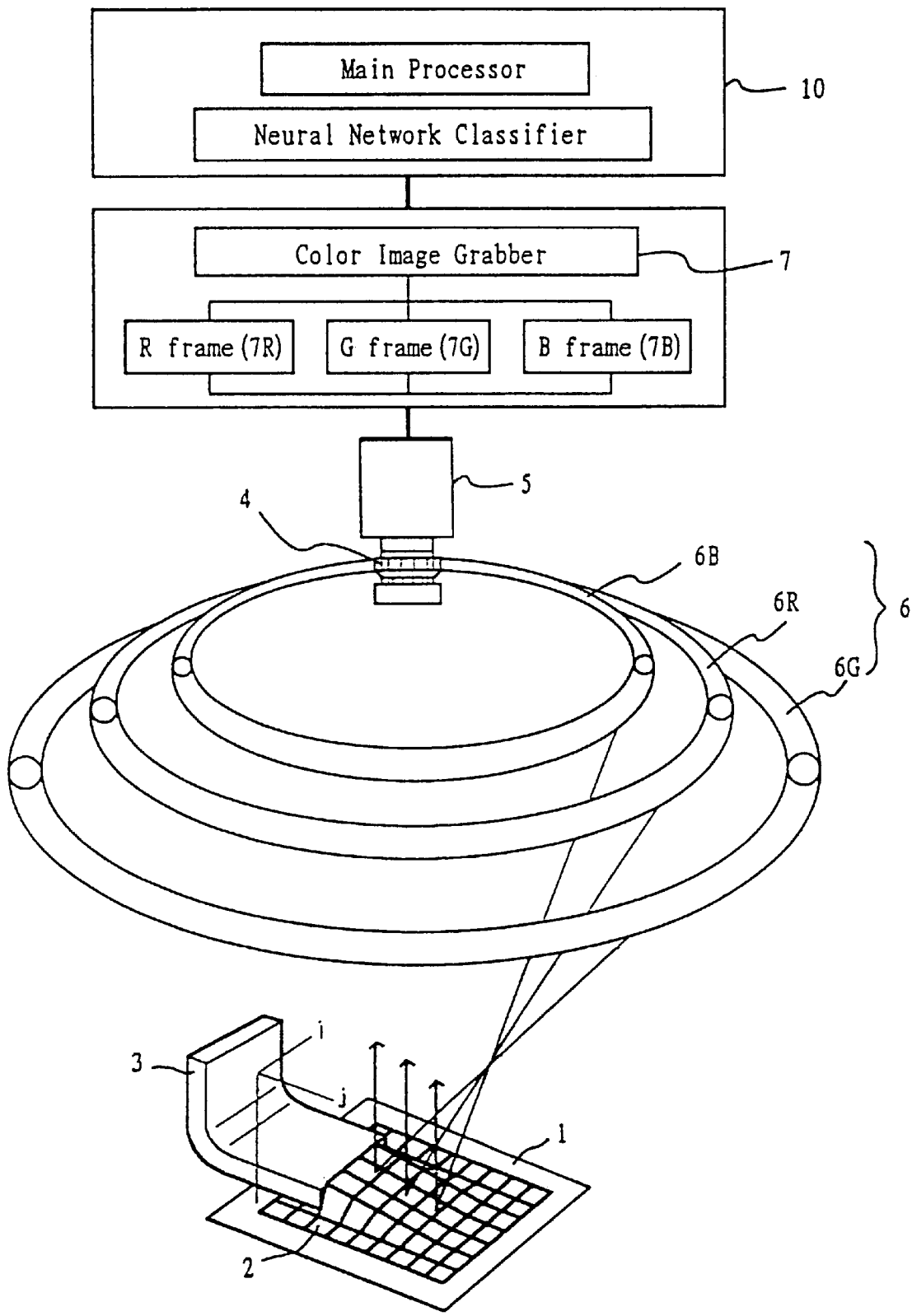
FIG. 1 is a diagram schematically showing an apparatus for inspecting a solder joint using a correlation neural network, in accordance with an embodiment of the present invention.

Referring to FIG. 1, the apparatus for inspecting a solder joint using a correlation neural network of the present invention is broadly divided into a solder joint image extracting portion and a solder joint shape classifying portion.

The solder joint shape extracting portion includes a color camera 5, a three-color illuminator 6, and a color image grabber 7. The three-color illuminator 6 consists of green, red and blue circular lamps 6G, 6R and 6B, respectively, which are coaxially tiered in sequence from the bottom of the inspection area 1 to emit the green, the red and the blue rays at different incident angles. When the three-color illuminator 6 is turned on, color images are reflected from a solder joint 2 and a lead 3, and introduced into the color camera 5 through a zoom lens 4. The color camera 5 captures the color images by, for example, a charge coupled device (CCD) type image pickup device. The color image grabber 7 grabs a red frame 7R, a green frame 7G and a blue frame 7B from the output of the color camera 5.

In the preferred embodiment of the present invention, the blue, the red and the green lamps 6B, 6R and 6G have diameters of 40 mm, 70 mm, and 130 mm, respectively.

The circular lamps 6B, 6R and 6G of the present invention can be assumed as distributed point light sources which are circularly located around a surface patch. If the diameters of the circular lamps 6B, 6R and 6G are larger than the size of the surface patch, the distributed point light sources can be assumed to illuminate the surface patch with the same polar angle. If the surface of the solder joint 2 is specular and such directional illumination is given, a specular reflection, either a point like highlight or a gloss contour, will appear in the image. When this occurs, some patches on the surface must be oriented such that the surface normal bisects the angle defined by the point light source, the given surface point and the viewer. This alignment is referred as the specularity condition. In the case of the circular lamps, the specularity condition is not only met at a point but also at the loci of points where the surface normal has constant inclination to a selected reference vector. Therefore, the specular surface patches with the same inclination relative to the reference vector exhibit the same color intensity as viewed from the camera 5 mounted at the top. Since the color lamps 6B, 6R and 6G illuminate the inspection area 1 with different incident angles, the specularity conditions generated by each lamp are different.

Figure 2A:
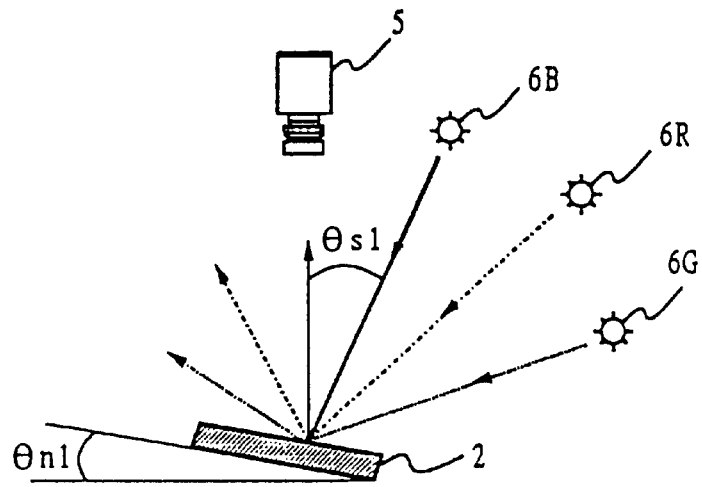
FIGS. 2A, 2B and 2C are views illustrating three different specularity conditions according to the configuration of color lamps and surface inclination.
Figure 2B:
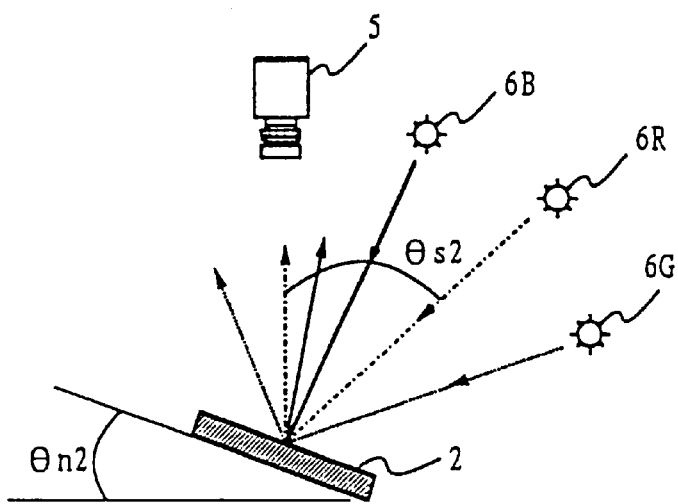
Figure 2C:
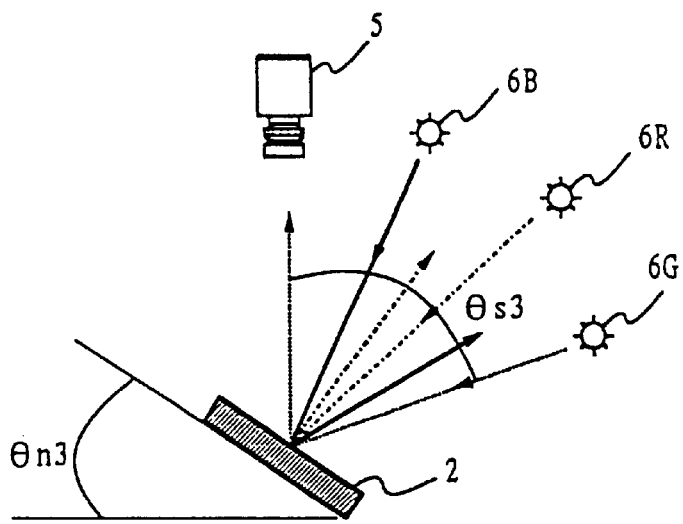

FIGS. 2A–2C shows three different specularity conditions according to the configuration of the color lamps and the surface inclination. For the blue circular lamp 6B in FIG. 2A, the slope of $\theta_{n1}$ which is nearly flat, meets the specurality condition such that the solder joint with this slope appears as a blue highlight pattern in a camera image. Other rays emitted from the red and green lamps 6R and 6G are not admitted into the camera principal direction such that the camera 5 can not capture the rays reflected on the surface as shown in FIG. 2A. For the red circular lamp 6R in FIG. 2B, the moderate slope of $\theta_{n2}$ satisfies the specularity condition such that the solder joint surface with this slope in FIG. 2B appears as a red highlight pattern in a camera image. In the same manner, for the green circular lamp 6G in FIG. 2C, the slope of $\theta_{n3}$ which is steep satisfies the specularity condition such that the solder joint surface with this slope in FIG. 2C appears as a green highlight pattern in a camera image. According to this principle, the three-dimensional geometry of the solder joint 2 can be represented by various-shaped patterns with blue, red, and green colors in the camera image.

In the preferred embodiment of the present invention, slopes $\theta_{n1}$, $\theta_{n2}$ and $\theta_{n3}$ of the inclined surfaces of the solder joints are about 10°, 20° and 35°, respectively. Also, incident angles, $\theta_{s1}$, $\theta_{s2}$ and $\theta_{s3}$ of the blue, the red and the green circular lamps 6B, 6R and 6G are set to 20°, 40° and 70° from the center axis of the camera 5, respectively.

While the specular surfaces, such as the lead 3 and the solder joint 2, reflect distinct color patterns, that is, the red, the green and the blue according to their surface inclinations, other rough surfaces, such as a plastic package of an electrical part and a PCB base plate, randomly diffuse the incident rays in all directions, thus mixing the colors of incident rays so that the reflections appear as their natural color in white light.

FIG. 7 shows typical synthetic examples of three-dimensional joint shapes and the corresponding highlight color patterns in images classified by their soldering qualities. The qualities of solder joints are divided into five classes; insufficient soldering, insufficient but acceptable soldering, acceptable soldering, excess but acceptable soldering, and excess soldering. The image is obtained by positioning a solder joint within a pre-defined window, in which the schematic color patterns are produced by thresholding a raw color image. The characteristics of the three-dimensional shape and the corresponding color pattern according to the classes of solder joint quality are described below.

(1) The insufficient soldering has a near flat solder fillet or very small fillet. As a result, blue pattern dominantly appears in the window image.

(2) As the amount of solder increases, joint surface begins to form a fillet which joins the lead and the solder pad. Since the insufficient but acceptable soldering has a small fillet, the red and green patterns begin to appear though their sizes are still small.

(3) The acceptable solder joint has a larger fillet than those of the previous two soldering classes and looks like a concave solder fillet. Thus, the green, red and blue patterns appear sequentially from the lead. This indicates that the surface near to the lead is inclined steeply and the joint surface connected with the solder pad is nearly flat.

(4) The excessive but acceptable soldering usually has an inclined flat surface, such that the red pattern appears dominantly in the window image.

(5) The excessive solder joint has a convex solder fillet so that the blue pattern is enclosed by the red and green color patterns. The sequence of color patterns from the lead is different from those of the other soldering classes.

The visual cues presented in the above are the spatial relation between color patterns, and are somewhat distinct. The visual cues used herein have two main features, that is, the area of each color pattern and the relative positions between each pair of color patterns.

In FIG. 1, the solder joint shape classifying portion comprises a correlation neural network 10.

Referring to FIG. 3, there is illustrated one example of the architecture of the correlation neural network 10. The correlation neural network 10 includes a preprocessing module 10A and a trainable module 10B. The preprocessing module 10A includes a plurality of input nodes 11 capable of receiving one-dimensional vector sequences, and a plurality of correlation nodes 12 for calculating a cross-correlation value and an auto-correlation value of the vectors sequences. The preprocessing module 10A converts the raw color image information extracted from the color image grabber (7 in FIG. 1) to a more simple form of information suitable for the inspection of the solder joint, and calculates the correlation values. In the preprocessing module 10A, raw color images are expressed as a simple representation, i.e., a series of vectors, G(i), R(i) and B(i).

The trainable module 10B includes two-stage calculation nodes 14 and 15. The trainable module 10B calculates an error and an average error for each sample pattern from the correlation values calculated from the preprocessing module 10A. Then, the trainable module 10B is trained based on the generalized-delta rule, and finally learns the classification criteria to supervise the solder joint inspection. A simple connection node 13 of the trainable module directly receives the values calculated from each correlation node of the preprocessing module 10A.

Figure 4:
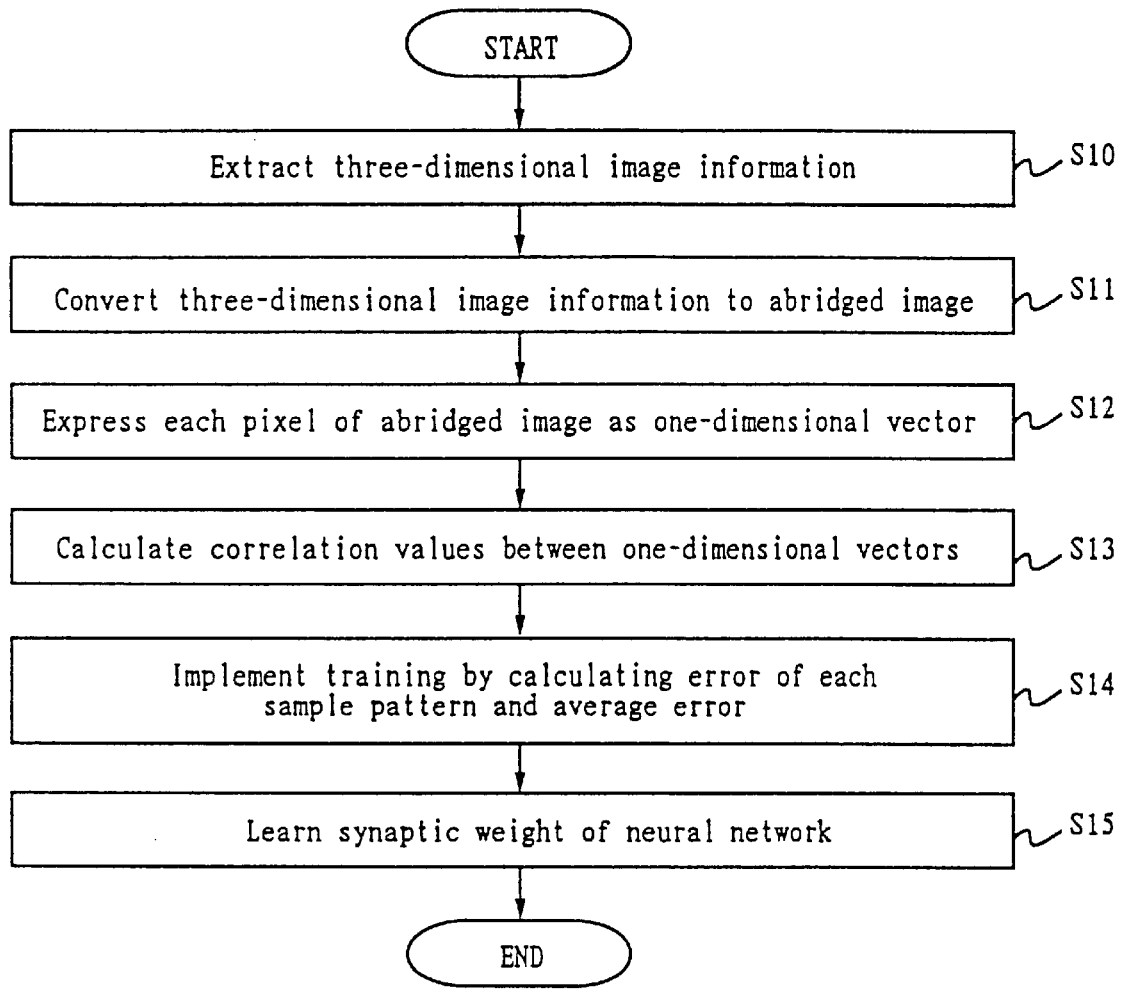
FIG. 4 is a flow chart explaining a method for inspecting a solder joint using a correlation neural network, in accordance with another embodiment of the present invention.

Referring now to FIG. 4, there is illustrated a flow chart showing a method for inspecting a solder joint using a correlation neural network, in accordance with another embodiment of the present invention. The method includes a preprocessing process for converting three-dimensional image information for the solder joint to a more simple form of information suitable for the inspection of the solder joint; and a training process for training the synaptic weights of the neural network for the limited set of training samples by comparing output values calculated from the preprocessing process with target values determined by a network designer.

To be more detailed, the three-dimensional image information is extracted under the three-color illuminator (step S10), and the extracted three-dimensional image information of the solder joint is converted to an abridged image (step S11). Each column of pixels of the abridged image is expressed as a one-dimensional vector (step 12). Correlation values between the one dimensional vectors are calculated (step S13). Training to calculate an error for each sample pattern and an average system error is implemented by comparing the output from the trainable module acting on the calculated vector correlation values with target values determined by the network designer (step S14). The synaptic weights of the neural network are learned using the obtained error and the average error (step S15).

Figure 5A:
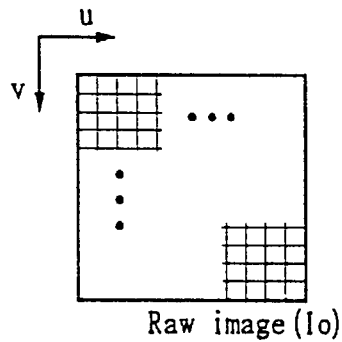
FIGS. 5A and 5B are views schematically illustrating a raw image and an abridged image.
Figure 5B:
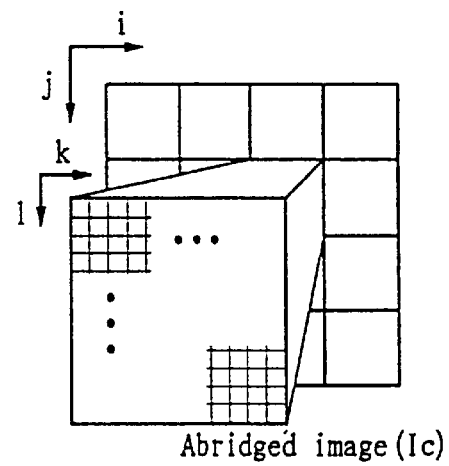

FIG. 5A illustrates a raw image $I_o(u, v)$, and FIG. 5B illustrates an abridged image $I_c(i, j)$ and a portion of the raw image within the abridged image. Symbols (u, v), (i, j) and (k, l) designate pixel coordinates of the raw image, the abridged image, and the portion of the raw image within the abridged image, respectively.

Figure 6:
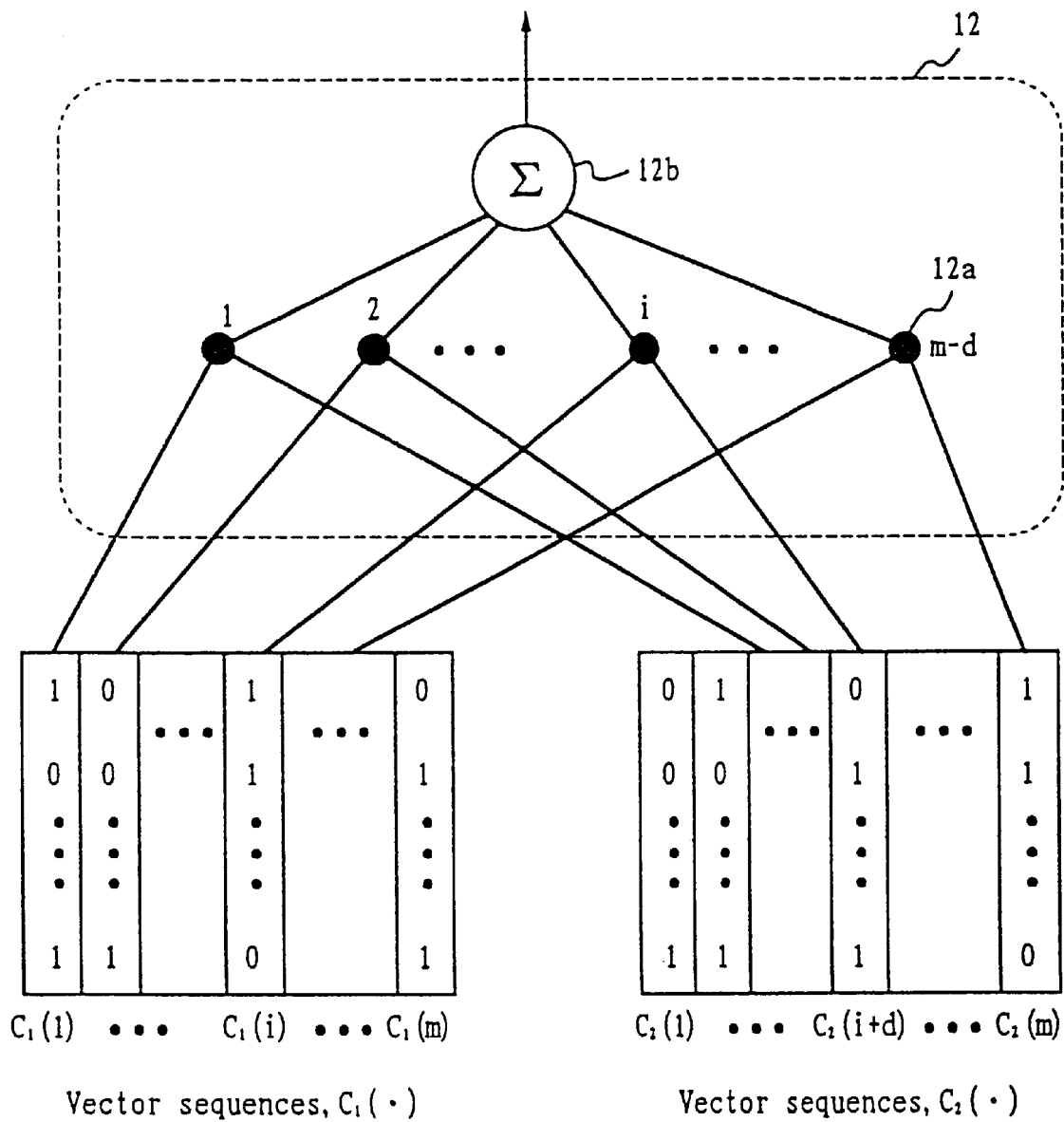
FIG. 6 is a diagram illustrating a correlation node of the correlation neural network of FIG. 3.

FIG. 6 illustrates a detailed diagram which shows the correlation node of the correlation neural network. There are shown two color vector sequences $C_1$ and $C_2$ which have one-dimensional vectors vectorized from the three-dimensional color image information through the vetorizing process of the preprocessing module, and the correlation node 12 for calculating the correlation values between the vectors. The correlation node 12 includes a cross product operator 12a and a sum operator 12b.

The correlation calculating process and the training process using the correlation values, which are carried out by the correlation neural network for the inspection of the solder joint, will be fully described in below. The method for inspecting a solder joint using a correlation neural network of the present invention can be broadly divided into an image pattern processing operation by the preprocessing module 10A and a training operation by the trainable module 10B, as shown in FIG. 3.

The preprocessing module 10A for converting the color image information to the simple information executes the image abridging step S11, the abridged image vectorizing step S12 and the correlation value calculating step S13, as shown in FIG. 4. The correlation node is defined to calculate cross-correlation and auto-correlation of the series of vectors which represent the spatial relation between the color patterns in the raw image. The geometric correlations yield the nonlinear combinations of color pixels in the raw image, and directly loaded to the trainable module 10B. The trainable module 10B then is trained based on the generalized-delta rule and finally learns the classification criteria to supervise the solder joint inspection.

FIG. 5 shows the image abridging step. At the image abridging step (S11 of FIG. 4), a raw color image $I_o(u, v)$ is converted to an abridged image $I_c(i, j)$ composed of fewer pixels. One pixel of the abridged image $I_c$, as shown in FIG. 5B, is set to be equivalent to a L×K pixel window of the raw image $I_o$, which can then be described by $$I_c(i, j) = 1, \text{ if } \sum_{l=0}^{L} \sum_{k=0}^{K} I_0(u_0 + l, v_0 + k) > \tau$$

$$= 0, \text{ else}$$

where, $(u_0, v_0)$ is the initial pixel of the raw image within a pixel $(i, j)$ of the abridged image, and $\tau$ is a threshold value which is determined by a network designer. The size of the abridged image, i.e. the number of pixels in an abridged image, ranges from the same size as a raw image to the size of one pixel. The full size may be prohibited because it imposes a large computational burden. As far as one abridged image maintains the spatial relation of its color patterns, its size is desired to be as small as possible. If the size of the abridged image is small, processing time is reduced, but classification accuracy is deteriorated. Therefore, a minimum size of the abridged image should be determined according to the difficulty in classifying an object, as will be readily understood from the experimental investigation for which results are presented in FIGS. 9 through 11.

At the abridged image vectorizing step of the preprocessing (S12 in FIG. 4), green, red and blue abridged images are rewritten as a sequence of one-dimensional vector formations which are denoted by $\{G(i)|i=1, \ldots, m\}$ $\{R(i)|i=1, \ldots, m\}$ $\{B(i)|i=1, \ldots, m\}$ as shown in FIG. 3. For example, a n×m blue abridged image, $\{I_c^b(i,j)|i=1, \ldots, m; j=1, \ldots, n\}$ can be rewritten as a sequence of column vector formations;

$B(i)=\{I_c^b(i,1), I_c^b(i,2), \ldots, I_c^b(i,n)\}, i=1, \ldots, m$ where the superscript b denotes the blue color. In the same manner, vectors R(i) and G(i) for red and green abridged images $I_c^r(i, j)$ and $I_c^g(i, j)$ can be obtained, respectively. FIG. 8. gives an example of vectorizing; FIG. 8A shows a 4×5 abridged image, and FIG. 8B shows the resulting vector sequences.

At the correlation value calculating step (S13 in FIG. 4), the spatial correlation values of certain combinations of the color vector sequences are calculated by using the correlation node (12 in FIGS. 3 and 6). The correlation node 12 includes a cross product operator 12a and a sum operator 12b. Assuming that the input to the correlation node 12 is two vector sequences $C_1(.)$ and $C_2(.)$, and a spatial correlation distance d, as shown in FIG. 6, the output of the correlation node is described by (output of correlation node)

$$= f[C_1(\cdot), C_2(\cdot), d] = \sum_{i=0}^{m-d} C_1(i) \cdot C_2(i+d)$$

where $\{C_1(i)|i=1, \ldots, m\}$ and $\{C_2(i)|i=1, \ldots, m\}$ are the two vector sequences to be calculated, and m is the maximum number of the vector sequences. The function of f[ ] is to calculate the product sum of pixels in the $C_1$-color abridged image and in the d-shifted $C_2$-color abridged image in the columnwise direction.

For example, if there are abridged images as shown in FIG. 8A, which are abridged in the image abridging step (S11 of FIG. 4), the vector sequences as shown in FIG. 8B can be expected as a result of the abridged image vectorizing step (S12 of FIG. 4). The output value of the correlation node 12 is then described by (output of correlation node)

$$= f[G(\cdot), R(\cdot), d] = \sum_{i=0}^{m-d} G(i) \cdot R(i+d).$$

The results of calculating the correlation nodes by changing the value of the correlation distance d, are as follows;

for d=1;

$f(G,R,1)=G(1)\cdot R(2)+G(2)\cdot R(3)+G(3)\cdot R(4)+G(4)\cdot R(5)=2$ for d=2;

$f(G,R,2)=G(1)\cdot R(3)+G(2)\cdot R(4)+G(3)\cdot R(5)=2$ for d=3;

$f(G,R,3)=G(1)\cdot R(4)+G(2)\cdot R(5)=0$ for d=4;

$f(G,R,4)=G(1)\cdot R(5)=0$

The correlation node is also applied to calculate an auto-correlation of a color vector sequence. The result of the node calculation is the sum of the high pixel of an abridged image which indicates the area of highlight blob in the image. It is described by (output of correlation node)

$$= f[C_1(\cdot), C_1(\cdot), d] = \sum_{i=0}^{m-d} C_1(i) \cdot C_1(i+d)$$

In this hypothetical case, the outputs of the preprocessing module represent the spatial relation of the red, the green and the blue patterns as to the geometrical correlations which are summarized by;

$$f[B(\cdot), R(\cdot), d], \quad d = 1, \ldots, m-1$$
$$f[R(\cdot), B(\cdot), d], \quad d = 1, \ldots, m-1$$
$$f[G(\cdot), R(\cdot), d], \quad d = 1, \ldots, m-1$$
$$f[R(\cdot), G(\cdot), d], \quad d = 1, \ldots, m-1$$
$$f[B(\cdot), G(\cdot), d], \quad d = 1, \ldots, m-1$$
$$f[G(\cdot), B(\cdot), d], \quad d = 1, \ldots, m-1$$
$$f[G(\cdot), G(\cdot), d], \quad d = 0$$
$$f[R(\cdot), R(\cdot), d], \quad d = 0$$
$$f[B(\cdot), B(\cdot), d], \quad d = 0$$

These calculation results yield an enhanced field which has more separable hyperplane according to the classes of the solder joints quality. Using such an enhanced field as input to the trainable module improves the performance of the trainable module, such that the learning rate is greatly increased and a simpler architecture of the trainable module with fewer layers and nodes suffices for classification.

FIG. 3 depicts the trainable module 10B. The trainable module 10B executes the synaptic weight training step (S14 in FIG. 4) for training the synaptic weights of the neural network by comparing the output from the trainable module acting on the correlation values calculated from the correlation value calculating step (S13 in FIG. 4) with target values determined by the network designer. The trainable module has a structure of a back propagation (BP) multi-layered neural network which captures the output values of the preprocessing module as input data for classification. The input nodes of the trainable neural network are constructed to receive 6×(m−1)+3 input values where the number of 6 corresponds to the number of cross-correlation terms, m−1 is the maximum number of correlation distances, and the number of 3 denotes the number of auto-correlation terms. The step uses the generalized-delta rule. The output $O_j$ of a node j is activated by using the sigmoid function as described by $$O_j = \frac{1}{1 + e^{-(net_j + \sigma_j)/\sigma_o}}$$

where $net_j$ is the net input to a node in layer j, the parameter $\sigma_j$ serves as a threshold or bias, and $sigma_o$ is a shape parameter. For the classification of solder joint image pattern, the output error $E_p$ for each sample pattern is taken as $$E_p = \frac{1}{2}(t_p - o_f)$$

where $t_p$ denotes the target classification values, and $o_f$ denotes the output generated by the neural network. The average system error E is defined as $$E = \frac{1}{2P} \sum_p (t_p - o_f)^2$$

where P is the number of input samples in the training set, and the subscript p denotes each sample. Convergence is achieved by using the generalized-delta rule. That is, $$\Delta w_{kj} = -\eta \frac{\partial E}{\partial W_{kj}} + \alpha$$

where η is the learning rate. In order to get better convergency of the network, a sort of momentum term with a momentum rate α is introduced. $W_{kj}$ is the synaptic weight connecting network node k with network node j.

To evaluate the performance of the method of the present invention, a series of experiments were performed for various solder joints. Firstly, the learning performance of the present method was investigated. Secondly, the classification performance was evaluated when Gaussian noises are added. Finally, tolerance to shift-distortion was tested. The series of experiments will be fully described below with reference to FIGS. 9 through 13.

Test samples of solder joint were prepared from commercially-manufactured PCBs. Experimental setup for preparing the samples is as follows. The color camera for capturing sample images has a 1:7 zoom lens giving the minimum and maximum fields of view, 4 mm(H)×3 mm(V) and 28 mm(H)×21 mm(V), respectively. An inspection field of view is set at 12 mm×9 mm on PCB, within which five or six solder joints are usually imaged. The color vision system digitizes a color image into 512(H)×512(V) pixels. The color intensities of each pixel are stored in three color frames of red, green, and blue with 256 normalized levels, respectively. Under this experimental setup, the 135 samples of a training set are prepared for five classes of solder joint quality such that a total of 27 samples is affiliated with each class for training and testing. To extract a sample solder joint window image, a solder joint window size of 60×75 pixels is used. The solder joint part within this pre-defined window usually consists of 47×56 pixels.

In the present method, there is a trade-off between the size of the abridged image and the classification performance of the trainable module. The smaller the size of the abridged image is, the smaller the memory size of the trainable module becomes. However, in this case, the classification accuracy gets worse. Therefore, as long as the classification accuracy is sufficient, it is desirable to reduce the memory size of the trainable module. In the experiment, three abridged image sizes of 4×5, 8×10 and 12×15 which are abridged from the 60×75 size raw image, are tested.

Figures 9A, 9B:
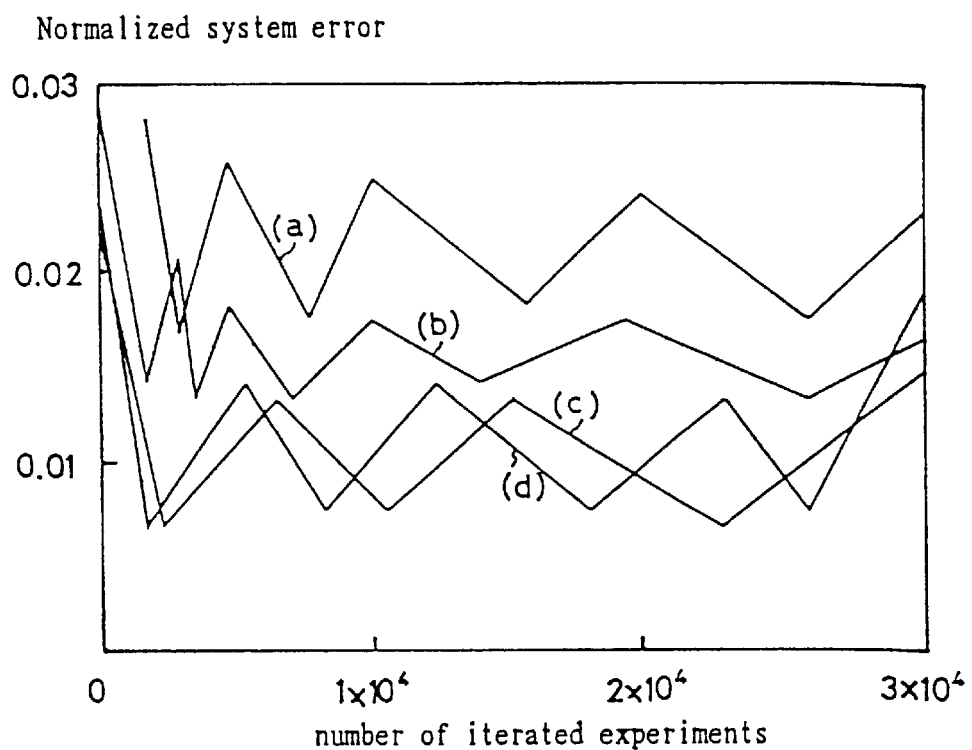
FIGS. 9A and 9B, 10A and 10B, and 11A and 11B show the training convergence of four candidate trainable modules in the neural network for abridged image sizes of 4×5 (FIGS. 9A and 9B), 8×10 (FIGS. 10A and 10B), and 12×15 (FIGS. 11A and 11B)
Figures 10A, 10B:
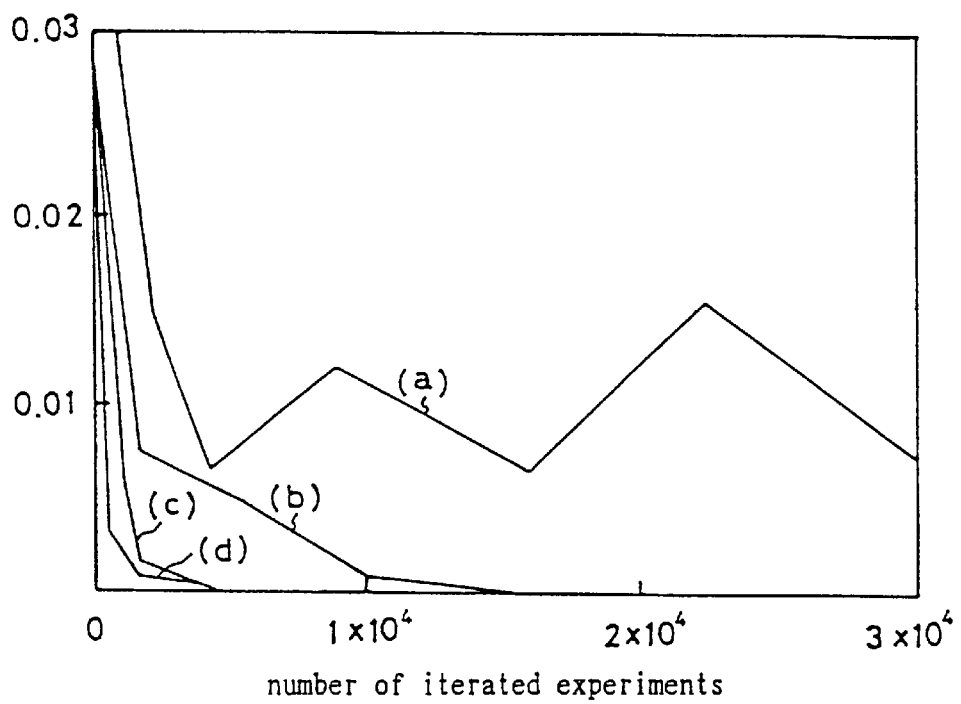
Figures 11A, 11B:
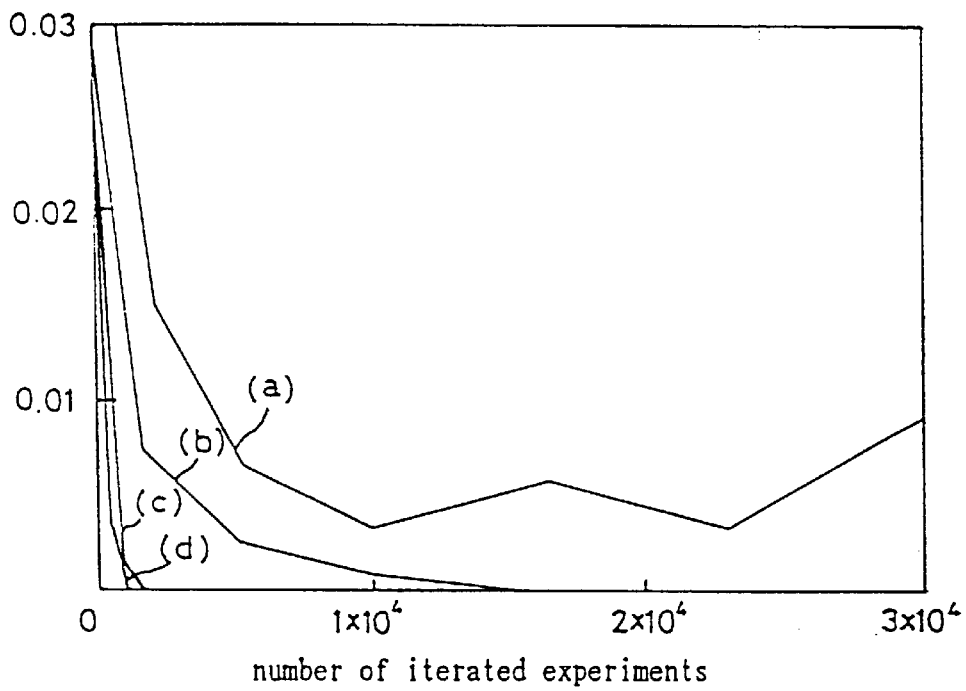

Since the output of the preprocessing module yields an enhanced representation of a raw image data, the architecture of the trainable module can be made simple. To examine this effect, four different kinds of BP neural network architectures from simple to complex are considered: a) a flat network without a hidden layer; b) a network with a single hidden layer having 5 nodes; c) a network with a single hidden layer having 10 nodes; and d) a network with two hidden layers having 4 nodes for each layer. For the four cases, the number of output nodes is commonly fixed at five—equivalent to the number of quality classes. The desired responses of the output nodes used in the training are given by;

(1, 0, 0, 0, 0) for the insufficient class (0, 1, 0, 0, 0) for the insufficient but acceptable class
(0, 0, 1, 0, 0) for the acceptable class
(0, 0, 0, 1, 0) for the excessive but acceptable class
(0, 0, 0, 0, 1) for the excessive class The neural networks are trained to minimize the error between the target and the output of the network by using the generalized-delta rule. FIG. 9 shows the training convergence of the four different kinds of BP network architecture for the 4×5 abridged image. The normalized system errors fluctuate slowly for the four kinds of BP networks, and eventually do not converge, although the learning rate and the momentum of inertia are changed. From these results, it can be found that the 4×5 abridged image is too coarse to represent the raw color image. One abridged image may belong to more than one class of the joint quality. FIG. 10 shows the training convergence of the neural networks for the 8×10 abridged image. For a flat net, the system error does not converge. For a net with one hidden layer, the convergency becomes better as the number of nodes in a hidden layer increases. A network with two hidden layers can not improve the training convergence. FIG. 11 shows the training convergence in the neural networks for the 12×15 abridged image. The training convergence in this case has the same trend as the case of the 8×10 abridged image. Overall convergence rates of this case are better than those of the 8×10 abridged image.

From the experiments, the size of abridged image is recommended to be over 8×10 pixels, while the architecture of the trainable module is recommended to have one hidden layer.

Figure 12:
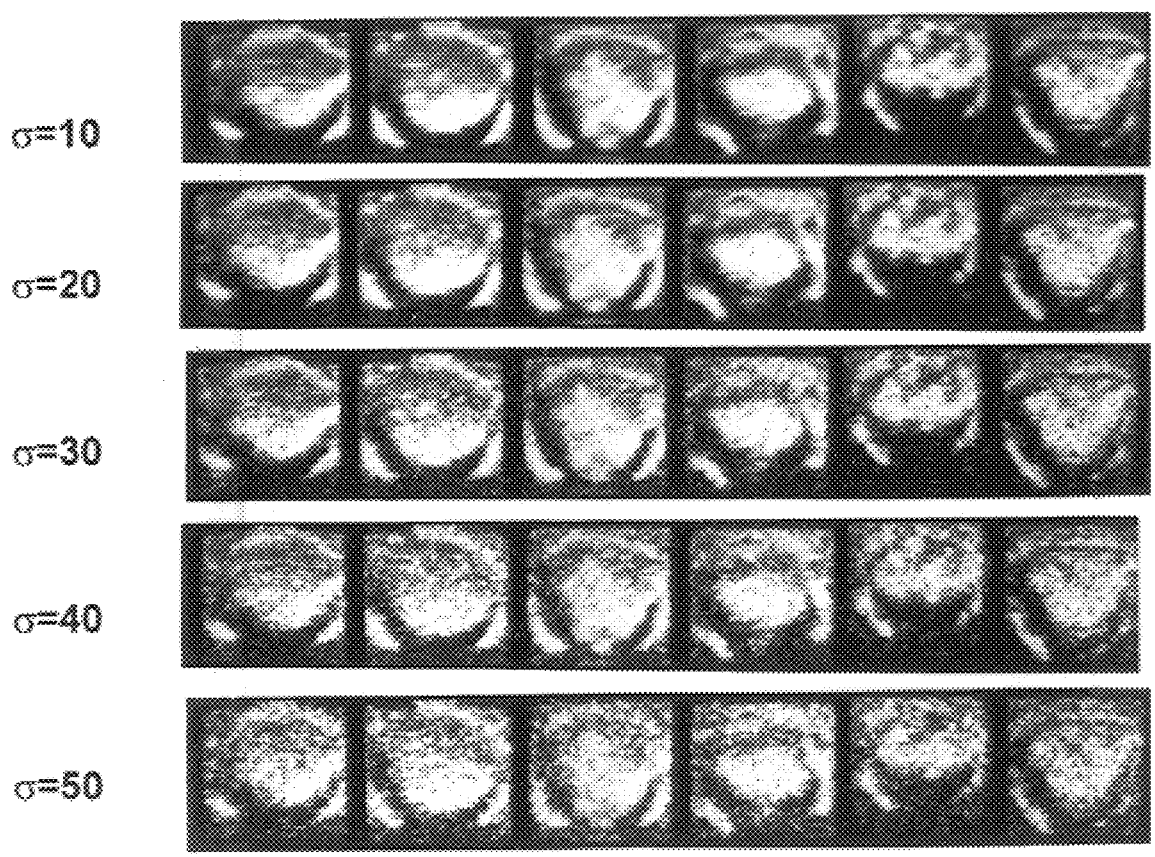
FIG. 12 shows example images of solder joints with added Gaussian noises.

To test classification performance of the present method, the success rate of classification with noisy images of the training data is evaluated. The training sample images are modified by adding Gaussian noise with a zero mean value and a standard deviation of between 0 and 50. The intensity values of the modified sample data are limited within the value of 0–255. FIG. 12 shows the example solder joint window images with added Gaussian noises, in which the solder joints belong to the acceptable class. Tests are carried out for the three different abridged image sizes, 4×5, 8×10 and 12×15.

Classification results are compared with those of a BP network without the correlation calculation step of the preprocessing stage. The architecture of the BP network consists of 5 output nodes, one hidden layer with 120 nodes, and 240 input nodes (8×10×3) capturing all pixels of the 8×10 abridged color image. For the 8×10 abridged image, the training convergence of the BP network is similar to the case of the proposed net having one hidden layer with 5 nodes. The memory size of weights in the BP network is, however, much larger than that used in the proposed net, since the number of input nodes in the BP network is 240 while that of the proposed net is 51.

Figure 13A:
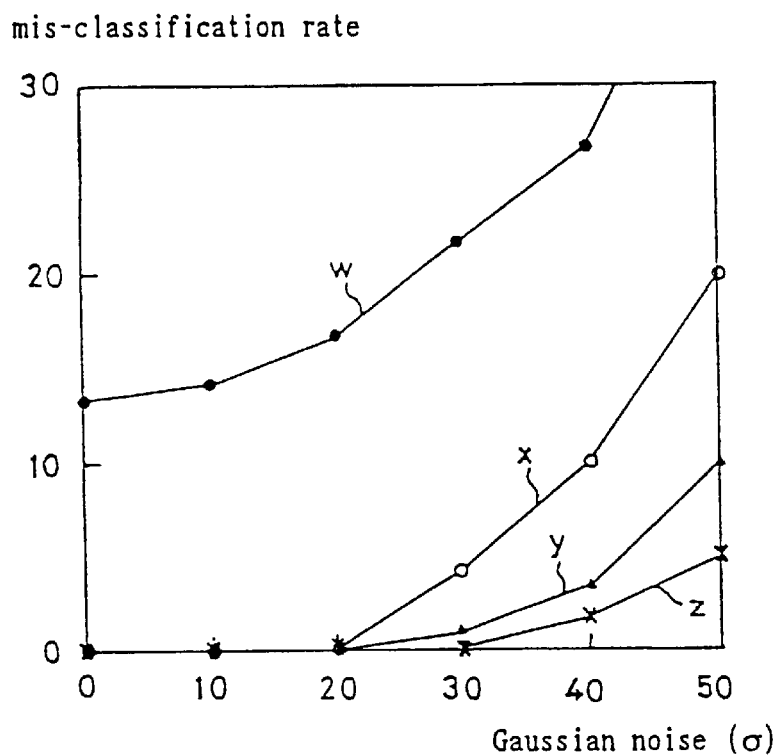
FIGS. 13A and 13B illustrate the classification performance of the method of the present invention for 4×5 abridged image size (w), 8×10 abridged image size (y), 12×15 abridged image size (z), and a general neural network operating without preprocessing (x).

FIG. 13A shows the success rate of classification when Gaussian noise is added to sample images. The two networks, the 8×10 abridged image (y) and the 12×15 abridged image (z) show 100% classification accuracy up to a standard deviation of 25. The BP network (x) without correlation calculations in the preprocessing stage is performed with 100% accuracy up to standard deviation 20; but, for a standard deviation greater than 20 is found to be inferior to the cases of (y) and (z). Compared with the BP network (x), the proposed networks having the abridged image size larger than 8×10 shows equivalent or superior results of classification. The network for 4×5 abridgment level did not classify the test samples even of noise free images with 100% success rate. A small size abridged image can not guarantee a good success rate of classification because it might lose too large a part of the information in the raw images.

One of difficult problem in classifying the color patterns is the position shift of the solder joint image. The color patterns are usually obtained from a pre-defined solder joint window image fitted over a solder pad on a PCB. Within the window, the solder joint often is not located at a fixed position. During the heating process which melts solder around the lead of the electrical part, the electrical part may be slightly floated. Floating shifts of the electrical part may arise in two different types—a translation shift and a rotation shift. Rotation is usually small enough to be ignored. If rotation occurs to some extent, the lead of the electrical part is very much displaced in the pre-defined window. This case must be excluded before the inspection process. Translation occurs frequently. Although solder joint is slightly translated within the pre-defined window, if the spatial relation of color patterns are not changed, quality of the solder joints is considered to be the same.

Figure 13B:
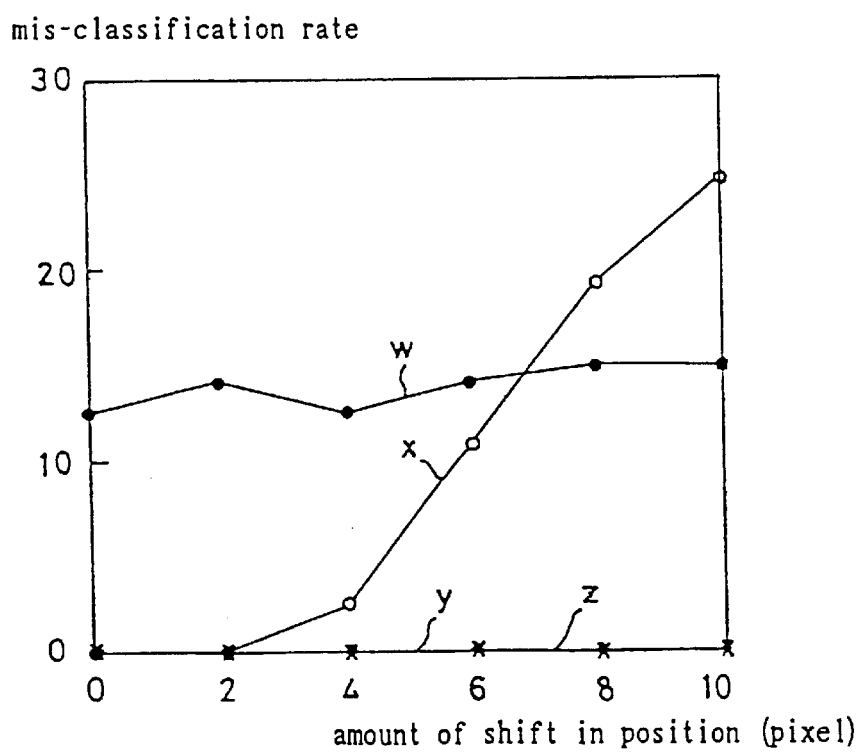

To test the tolerance of the proposed method to translation shift in position, sample images of solder joint with size of 47×56 are shifted up to 10 pixels within the window image with size of 60×75. No Gaussian noise is added to the image. FIG. 13B shows the success rate of classification for the images shifted in position by translation. The preferred methods of case (y) for 8×10 level and case (z) for 12×15 level classify the shifted test samples without confusion. However, the miss-classification rate of the BP network (x) without the correlation calculations in the preprocessing stage rapidly increases as the position shift increases. From these experimental results, it is to be concluded that the proposed method yields shift-invariant classification of solder joint images.

Compared with other high order neural network approaches, the proposed method uses smaller size memory for synaptic weight storage. Generally, to recognize a pattern shift-invariantly, high order neural network approaches have been adapted. To construct an original second-order correlation neural network for a N×N pixel image, the required number of input nodes are $_{N\times N}C_2$. Thus, in the case of the 8×10 color image, the number of input nodes are (8×10× 3)-choose-2 or 57369. It is unfeasible for practical use due to the limitation of computer hardware memory.

As described above, the method and apparatus for inspecting a solder joint using a correlation neural network according to the present invention have advantages as follows.

(1) Solder joint images can be effectively classified regardless of shift in position within a pre-defined window.

(2) Compared with a BP network without correlation calculations, smaller memory storage for synaptic weights is required and learning rate is improved.

(3) Color image processing inherently requires a complex processing system due to its large data size and color adjustment. Overcoming this barrier, the geometric correlation terms represent the spatial relations of red, green and blue color patterns in an effective manner.

(4) In complex classification problems, it is sometimes inefficient if a neural network such as a BP network accomplishes the whole classification task without other help. In the present invention, the experiences of a human inspector to determine the classification hierarchy and the amount of image abridging is utilized to reduce the classification burden from that of the BP network without preprocessing. As a result, the whole classification performance of the network is improved.

While the present invention has been described and illustrated with reference to preferred embodiments thereof, those skilled in the art should understand that the present invention is not limited to these embodiments, and that various changes and modifications can be made therein without departing from the spirit and scope of the invention as defined in the appended claims and their equivalents.

What is claimed is:

1. An apparatus for inspecting a solder joint, said apparatus comprising:
   a solder joint image extracting means for extracting three-dimensional image information of a solder joint subjected to multi-color illumination; and
   a solder joint shape classifying means for learning a classification hierarchy of solder joint images by using a training set of said solder joint images classified into said classification hierarchy by a human solder joint inspector, and for applying said learned classification hierarchy to said extracted image information, said solder joint shape classifying means including a preprocessor which converts said three-dimensional image information into a plurality of one-dimensional vector sequences, each one-dimensional vector sequence being for one color of the multi-color illumination and for a one-dimensional spatial extent, calculates correlation values among all combinations of said one-dimensional vector sequences, and supplies said correlation values as said training set.

2. An apparatus for inspecting a solder joint as claimed in claim 1, wherein said solder joint image extracting means comprises:
   a multi-color illuminator for emitting at least three colors of light, each color at a different incident angled onto a solder joint inspection area;
   a color camera for capturing color images reflected from said solder joint inspection area with a digital image pickup device; and
   a color image grabber for grabbing a plurality of color frames, one frame for each of said colors, from an output of said color camera.

3. An apparatus for inspecting a solder joint as claimed in claim 2, wherein said solder joint shape classifying means comprises:
   a correlation neural network for converting said plurality of color frames into said plurality of one-dimensional vector sequences, for calculating said correlation values among said vector sequences, for learning synaptic weights to apply to said correlation values to produce said classification hierarchy determined by said human solder joint inspector, and for applying previously learned said synaptic weights to said correlation values to produce an automatic classification within said classification hierarchy.

4. An apparatus for inspecting a solder joint as claimed in claim 3, wherein said correlation neural network comprises:
   a trainable module for learning synaptic weights to apply to said correlation values to produce said classification hierarchy determined by said human solder joint inspector, and for applying previously learned said synaptic weights to said correlation values to produce an automatic classification within said classification hierarchy.

5. An apparatus for inspecting a solder joint as claimed in claim 2, wherein said multi-color illuminator comprises:
   three circular, high-frequency neon lamps respectively emitting green light, red light, and blue light, which are coaxially tiered in sequence of decreasing diameter and in sequence of increasing distance from a plane containing said solder joint inspection area.

6. An apparatus for inspecting a solder joint as claimed in claim 5, wherein said green, red, and blue circular, high frequency neon lamps have diameters of about 130 mm, about 70 mm, and about 40 mm, respectively.

7. An apparatus for inspecting a solder joint as claimed in claim 5, wherein said green, red and blue circular high frequency neon lamps are positioned to have incident angles at said solder joint inspection area of about 70°, about 40° and about 20° from an imaging axis of said color camera, respectively.

8. An apparatus for inspecting a solder joint, said apparatus comprising:
   a color camera for capturing, with a digital image pickup device, color images reflected from said solder joint located in a solder joint inspection area;
   three circular, high-frequency neon lamps, one emitting green light, the next emitting red light, and the last emitting blue light;
   a color image grabber for grabbing a plurality of color frames, one frame for each of said plurality of colors, from an output of said color camera; and,
   a correlation neural network comprising a preprocessing module for calculating correlation values among a plurality of one-dimensional vector sequences derived from said plurality of color frames within one image, each one-dimensional vector sequence being for one color of the plurality of color frames and for a one-dimensional spatial extent, and a trainable module for learning synaptic weights to apply to said correlation values to produce a classification hierarchy determined by a solder joint inspector, and for applying previously learned said synaptic weights to said correlation values to produce an automatic classification within said classification hierarchy.

9. A method for inspecting a solder joint, comprising:
   illuminating a solder joint with multiple-color light emitters distributed in three-dimensions;
   extracting a multi-colored image of said solder joint;
   determining a classification hierarchy of said solder joint by a human solder joint inspector;
   classifying solder joint images by training a solder joint shape classifier to associate said extracted images of said solder joint with said classification hierarchy, and by applying said trained solder joint classifier to said extracted images of said solder joint, said classifying including converting said multi-colored image into a plurality of one-dimensional vector sequences, each one-dimensional vector sequence being for one color of the multi-color illumination and for a one-dimensional spatial extent, calculating correlation values among all combinations of said one-dimensional vector sequences, and using said correlation values for said training.

10. A method for inspecting a solder joint as claimed in claim 9, wherein said illuminating of a solder joint with multiple-color light in three dimensions comprises placing different color illuminators at different angles of incidence to a solder joint inspection area.

11. A method for inspecting a solder joint as claimed in claim 10, wherein said placement of different color illuminators at different angles of incidence to a solder joint inspection area comprises placing three circular light emitters of green, red, and blue light, coaxially in order of decreasing diameter and in sequence of increasing distance from said solder joint inspection area.

12. A method for inspecting a solder joint as claimed in claim 9, wherein said extracting of a multi-colored image of said solder joint comprises capturing a digital image of light reflected from a solder joint inspection area, and grabbing a plurality of color frames from said digital image.

13. A method for inspecting a solder joint as claimed in claim 9, wherein said classifying of solder joint images comprises operating a correlation neural network to learn to associate said extracted images of said solder joint with said classification hierarchy, and to act on said extracted images of said solder joint to produce an automatic classification within said classification hierarchy.

14. A method for inspecting a solder joint as claimed in claim 13, wherein operating of the correlation neural network comprises:
  training synaptic weights of a trainable module to convert said correlation values into said classification hierarchy by comparing the network output to classifications made by said human solder joint inspector; and
  applying the learned synaptic weights from said training to classify said multi-colored image of said solder joint within said classification hierarchy.

15. A method for inspecting a solder joint as claimed in claim 14, wherein said classifying further comprises:
  (a) abridging said multi-colored image into an abridged image which has a size smaller than said multi-colored image, said abridged image including a plurality of columns of pixels;
  (b) expressing each column of pixels of said abridged image as a set of one-dimensional vector sequences, the set including a one-dimensional vector sequence for each color of said multi-colored image, all of said sets of one-dimensional vector sequences comprising said plurality of one-dimensional vector sequences; and
  (c) forming said correlation values by calculating cross-correlation and auto-correlation values among said one-dimensional vectors sequences.

16. A method for inspecting a solder joint as claimed in claim 15, wherein said training comprises:
  (d) calculating a sample pattern error $E_p$ and an average system error E by comparing network output values with target classification values defined by said classification hierarchy; and
  (e) training said synaptic weights of said trainable module by using said sample pattern error and said average system error.

17. A method for inspecting a solder joint as claimed in claim 16, wherein in said calculating comprises,
  activating the output $O_j$ of a node j, where j indicates a layer of the correlation neural network in which the node is located, using sigmoid function as described by $$O_j = \frac{1}{1 + e^{-(net_j + \sigma_j)/\sigma_o}}$$

where $net_j$ is the net input to the node in layer j, the parameter $\sigma_j$ serves as a threshold or bias, and $\sigma_o$ is a shape parameter;
  said sample pattern error $E_p$ for each sample pattern is taken as $$E_p = \frac{1}{2}(t_p - o_f)$$

where $t_p$ denotes said target classification values, and $o_f$ denotes said network output values; and
  said average system error E is defined as $$E = \frac{1}{2P}\sum_p (t_p - o_f)^2$$

where P is a total number of said multi-colored images in a training set, and subscript $_p$ denotes each said multi-colored images in said training set.

18. A method for inspecting a solder joint as claimed in claim 16,
  wherein said training comprises achieving convergence for said synaptic weights using a generalized-delta rule according to the following equation;

$$\Delta w_{kj} = -\eta \frac{\partial E}{\partial W_{kj}} + \alpha$$

where $\eta$ is the learning rate, alpha is a momentum term, and $W_{kj}$ is said synaptic weight for the output from network node k, where k indicates a layer of the correlation neural network in which the node is located, when used as input to network node j, where j indicates a layer of the correlation neural network in which the node is located.

19. A method for inspecting a solder joint as claimed in claim 15,
  wherein said abridging includes setting one pixel of said abridged image to be equivalent to a window of a raw image, where said window is L pixels wide by K pixels high (L×K), and said raw image is one color of said multi-colored image of said solder joint, and then said one pixel of said abridged image is described by $$I_c(i, j) = 1, \text{ if } \sum_{l=0}^{L}\sum_{k=0}^{K} I_0(u_0 + l, v_0 + k) > \tau$$
$$= 0, \text{ else}$$

where, $(u_0, v_0)$ is a position of an initial pixel of said raw image within said one pixel of said abridged image at position (i, j) of said abridged image, l is an integer indicating a column number in said raw image, k is an integer indicating a row number in said raw image, i is an integer indicating a column number in said abridged image, j is an integer indicating a row number in said abridged image, and $\tau$ is a threshold value which is determined by a network designer;
  wherein said expressing includes rewriting green, red and blue abridged images as said one-dimensional vector sequences which are denoted by $$\{G(i)|i=1, \ldots, m\}$$
$$\{R(i)|i=1, \ldots, m\}$$
$$\{B(i)|i=1, \ldots, m\}$$

wherein said forming includes calculating spatial correlation values of certain combinations of color vector sequences by using a correlation node, the output of said correlation node being described by $$f\{C_1(\cdot), C_2(\cdot), d\} = \sum_{i=0}^{m-d} C_1(i) \cdot C_2(i+d)$$

where $\{C_1(i)|i=1, \ldots, m\}$ and $\{C_2(i)|i=1, \ldots, m\}$ are the two vector sequences to be calculated, d is a spatial correlation distance between the two vector sequences, and m is the maximum number of elements in each of said vector sequences.

* * * * *